United States Patent [19]

Martin

[11] Patent Number: 4,475,945
[45] Date of Patent: Oct. 9, 1984

[54] AMINOGLYOXYLOITRILE OXIMINO CARBOXYLIC ACID ESTERS AND THIO ESTERS FOR THE PROTECTION OF CROPS AGAINST INJURY BY HERBICIDES

[75] Inventor: Henry Martin, Allschwil, Switzerland

[73] Assignee: Ciba-Geigy Corporation, Ardsley, N.Y.

[21] Appl. No.: 425,782

[22] Filed: Sep. 28, 1982

Related U.S. Application Data

[60] Division of Ser. No. 112,049, Jan. 14, 1980, Pat. No. 4,416,686, which is a continuation of Ser. No. 938,205, Aug. 3, 1978, abandoned.

[51] Int. Cl.$^3$ .................... A01N 25/32; C07C 121/80
[52] U.S. Cl. ........................................ 71/105; 71/100; 260/465 D
[58] Field of Search ............... 260/465 D; 560/35; 564/254; 71/98, 105, 111, 121, 100

[56] References Cited

U.S. PATENT DOCUMENTS

| | | | |
|---|---|---|---|
| 3,492,333 | 1/1970 | Dickore et al. | 564/255 X |
| 3,522,287 | 7/1970 | Donninger et al. | 260/465.4 |
| 3,639,620 | 2/1972 | Donninger et al. | 424/304 |

FOREIGN PATENT DOCUMENTS

| | | |
|---|---|---|
| 2436655 | 2/1975 | Fed. Rep. of Germany . |
| 958631 | 5/1964 | United Kingdom . |
| 1207788 | 10/1970 | United Kingdom . |
| 1245397 | 9/1971 | United Kingdom . |
| 1273357 | 5/1972 | United Kingdom . |
| 1458355 | 12/1976 | United Kingdom . |
| 1460436 | 1/1977 | United Kingdom . |
| 1554708 | 10/1979 | United Kingdom . |

*Primary Examiner*—Dolph H. Torrence
*Attorney, Agent, or Firm*—Frederick H. Rabin

[57] ABSTRACT

Oxime carbamates and oxime carbonates of the formula

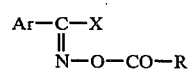

in which
Ar is optionally substituted phenyl, naphthyl, furan or thiophene,
X is hydrogen, carboxylic acid, alkanoyl, halogen or alkyl, and
R is mono- or di-substituted amine, an optionally substituted alkoxy or an optionally substituted alkylthio group, the substituents of which include optionally-substituted hydrocarbyl groups and heterocyclic groups are suitable as antidotes for the protection of cultivated plants against harmful agricultural chemicals, in particular against herbicides which are insufficiently compatible with the cultivated plants. These compounds can be used either on their own or together with the agricultural chemicals. One of the possibilities offered is the dressing or immersion treatment of seed or of seedlings, of the crop to be protected, with solutions or dispersions of said compounds.

5 Claims, No Drawings

AMINOGLYOXYLOITRILE OXIMINO CARBOXYLIC ACID ESTERS AND THIO ESTERS FOR THE PROTECTION OF CROPS AGAINST INJURY BY HERBICIDES

This is a division of application Ser. No. 112,049 filed on Jan. 14, 1980, now U.S. Pat. No. 4,416,686, which is a continuation of application Ser. No. 938,205, filed on Aug. 30, 1978, now abandoned.

The present invention relates to oxime carbamates and oxime carbonates of the general formula I

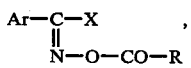

to novel compositions based on these compounds, and to the application of these compositions or compounds for the protection of cultivated plants against harmful agricultural chemicals.

The symbols in the formula I have the following meanings:

Ar is a phenyl group of the formula

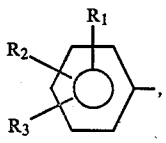

a naphthyl group which is substituted by $R_2$ and $R_3$, a furan or thiophene ring which is unsubstituted or substituted by halogen, $NO_2$ or lower alkyl, or Ar is one of the radicals —$COOR_4$ or —CO—$R_8$, X is —CN, lower alkanoyl, a carboxylic acid ester group, —COOH, hydrogen, a carboxylic acid amide group, halogen or lower alkyl, $R_1$ is hydrogen, halogen, lower alkyl, lower alkoxy, or a phenoxy group which is in the para-position and which is unsubstituted or substituted a maximum of twice by halogen, —CN, $NO_2$ or $CF_3$, $R_2$ and $R_3$ independently of one another are hydrogen, halogen, $NO_2$, lower alkyl, haloalkyl or lower alkoxy, $R_4$ is an aliphatic, cycloaliphatic or araliphatic group, and an aromatic radical can be substituted as defined under $R_2$ and $R_3$ and can be additionally substituted by —CN, R is either (a) a radical —$N(R_5)(R_6)$, in which $R_5$ is lower alkoxy or is the same as $R_6$, $R_6$ is hydrogen or an aliphatic, cycloaliphatic, araliphatic, aromatic or heterocyclic group, and an aromatic radical can be substituted as given under $R_2$ and $R_3$, or (b) a radical —$YR_7$, in which Y is oxygen or sulfur, and $R_7$ is one of the 5 groups given for $R_6$, $R_8$ is either (a) a radical —$N(R_9)(R_{10})$, in which $R_9$ is hydrogen, lower alkyl or cycloalkyl, and $R_{10}$ has the meaning of $R_6$ or is hydrogen, or $R_9$ and $R_{10}$ together with the —N atom form a 3-7-membered ring which can be substituted by lower alkyl groups, or (b) a radical —NH-CONH$R_{10}$.

Compounds of the formula I are accordingly (a) carbamates or (b) (thio) carbonates.

Halogen in the formula I is fluorine, chlorine, bromine or iodine.

Carboxylic acid esters are carboxylic acid lower alkyl esters. Carboxylic acid amides denote, besides —$CONH_2$, also monoalkyl-substituted or symmetrically or unsymmetrically dialkyl-substituted amides, with the alkyl groups being lower alkyl.

The term 'alkyl' on its own or as part of a substituent includes branched and unbranched $C_1$ to $C_8$ alkyl groups; lower alkyl denotes $C_1$-$C_4$ alkyl. Examples are methyl, ethyl, propyl, isopropyl, butyl, isobutyl, sec-butyl and tert-butyl, and also the higher homologues amyl, isoamyl, hexyl, heptyl or octyl, together with isomers thereof. Correspondingly, alkanoyls or cyanalkyls contain an additional C atom.

The term 'aliphatic group' includes radials which are saturated (alkyls) and also unsaturated (alkenyls, alkadienyls or alkynyls), which are halogen-substituted, cyano-substituted and interrupted by oxygen, and which contain a maximum of 8 carbon atoms. The term 'aromatic group' in the definition of the substituents $R_4$, $R_5$ and $R_6$ embraces phenyl and naphthyl. The term 'araliphatic radical' is to be interpreted in accordance with the two preceding definitions. An araliphatic radical includes an aryl group such as unsubstituted or mono- to tri-substituted phenyl, or naphthyl, whih is bound by way of lower alkyl or lower alkenyl to the radical of the molecule. Examples are benzyl, phenethyl or phenylallyl and also homologues.

The term 'heterocyclic radical' includes 5- to 10-membered ring systems having 1 or 2 rings and a maximum of 3 heteroatoms from the series N, O or S. $C_3$-$C_7$ cycloalkyl groups are cyclopropyl, cyclobutyl, cyclopentyl, cyclohexyl and cycloheptyl. Cycloaliphatic radicals correspond to these ring systems, but in addition they may contain, if structurally possible, one or more double bonds.

The arylglyoxylnitrile oximes of the general formula

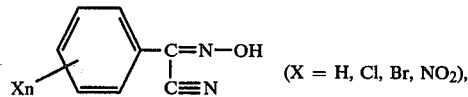

suggested in the U.S. Pat. No. 3,799,757, are insufficiently effective as growth inhibitors and plant-growth regulators; furthermore, they are not stable and decompose after a fairly short space of time. No herbicidal-antidote action has become known.

In comparison with the above compounds, oximes of the formula I are excellently suitable for protecting cultivated plants, such as cultivated millet, rice, maize, varieties of cereals (wheat, rye, barley or oats), cotton, sugar beet, sugar cane, soya bean, etc., from being attacked by agricultural chemicals harmful to plants, particularly by herbicides of the most varied classes of substances, such as triazines, phenylurea derivatives, carbamates, thiolcarbamates, haloacetanilides, halophenoxyacetic acid esters, substituted phenoxyphenoxyacetates and phenoxyphenoxypropionates, substituted pyridineoxyphenoxyacetates and pyridineoxyphenoxypropionates, benzoic acid derivatives, and so forth, in cases where these chemicals do not act selectively or do not act sufficiently selectively, that is to say, damage to a greater or lesser extent the cultivated plants in addition to destroying the weeds to be controlled. The invention relates also to compositions which contain these oxime derivatives of the formula I, together with herbicides.

There have already been suggested as antidotes various substances able to specifically antagonise the harmful action of a herbicide on the cultivated plant, that is to say, able to protect the cultivated plant without noticeably affecting the herbicidal action against the weeds to be controlled. Depending on its properties, an antidote of this kind (also called a safener) can be used for the preliminary treatment of the seed of the cultivated plant (dressing of the seed or of the seedlings); or it can be applied into the seed furrows before sowing; or it can be applied as a tank mixture, on its own or together with the herbicide, before or after emergence of the plants. The pre-emergence treatment includes both the treatment of the cultivated area before sowing (ppi=pre plant incorporation) and the treatment of the sown cultivated area before emergence of the plants.

Thus, the British patent specification No. 1,277,557 describes the treatment of seed and seedlings of wheat and sorghum with certain esters and amides of oxamic acid before the attack by N-methoxymethyl-2',6'-diethylchloroacetanilide (Alachlor). Other publications (German Offenlegungsschriften Nos. 1,952,910 and 2,245,471, and French patent specification No. 2,021,611) suggest antidotes for the treatment of cereals, maize seed and rice seed to protect them against attack from herbicidal thiolcarbamates. In the German patent specification No. 1,576,676 and U.S. patent specification No. 3,131,509, hydroxyaminoacetanilides and hydantoins are suggested for the protection of cereal seeds against carbamates, such as IPC, CIPC, and so forth. In further development, however, all these preparations have proved to be inadequate.

To be emphasised as antidotes are in particular those compounds of the formula I in which Ar is a phenyl or naphthyl radical as defined in the foregoing, and the other substituents have the following meanings: X is cyano, hydrogen, lower alkanoyl, a carboxylic acid ester group, a carboxylic acid amide group or lower alkyl, $R_1$ is hydrogen, halogen, or phenoxy group which is in the para-position and which is unsubstituted or substituted a maximum of twice by halogen, —CN or $CF_3$, $R_2$ and $R_3$ independently of one another are hydrogen, halogen, lower alkyl, haloalkyl or lower alkoxy, whilst Y and $R_5$, $R_6$ and $R_7$ have the meanings already defined. This subgroup is to be called compound group Ia.

Amongst these compounds of the group Ia, the group Ib constitutes one of the compound groups preferred as antidotes. Compounds of the group Ib are those of the formula I in which Ar is a phenyl group as defined in the foregoing, X is cyano, hydrogen, acetyl, —COO-lower alkyl, —COONH$_2$, —COONH-lower alkyl, —COON (lower alkyl)$_2$ or methyl, $R_1$ is hydrogen, $R_2$ and $R_3$ are hydrogen, halogen, lower alkyl, $CF_3$, methoxy or ethoxy, $R_5$ is hydrogen lower alkyl or lower alkoxy, $R_6$ is an aliphatic group, or a phenyl group which is unsubstituted or substituted by halogen, lower alkyl, $CF_3$, methoxy or ethoxy, Y is oxygen or sulfur, and $R_7$ has the meaning given above for $R_6$.

An important group of antidotes is formed by those compounds of the formula I in which Ar is a thiophene ring unsubstituted or substituted by halogen or lower alkyl, and in which the substituents X, Y, $R_5$, $R_6$ and $R_7$ have the meanings given for the compound group Ia, but preferably the meanings given for the compound group Ib.

A further important group of antidotes for the protection of cultivated plants against herbicides is the subgroup of the formula I in which Ar is one of the radicans —COOR$_4$ or —COR$_8$, wherein R$_4$ is a lower aliphatic group having a maximum of 4 C atoms or is phenyl, and in the definition of R$_8$ the substituents R$_9$ and R$_{10}$ independently of one another are hydrogen or lower alkyl, or phenyl unsubstituted or substituted by halogen, $CF_3$ or lower alkyl, whilst the substituents X, Y, R$_5$, R$_6$ and R$_7$ have the meanings given for the compound group Ia, but preferably have the meanings given for the compound group Ib.

Surprisingly, oximes of the formula I have the property of being able to protect cultivated plants against attack from agricultural chemicals harmful to plants, particularly against herbicides of the most varies classes of substances, including 1,3,5-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyacetates and phenoxyphenoxypropionates, substituted pyridinephenoxyacetates and pyridinephenoxypropionates, benzoic acid derivatives, and so forth, in cases where these chemicals are not compatible, or not sufficiently compatible, with the cultivated plants.

Depending on the purpose of application, such an antidote of the formula I can be used for pretreatment of the seed of the cultivated plant (dressing of the seed or of the seedlings), or can be applied to the soil before or after sowing, or can be applied on its own or together with the herbicide before or after emergence of the plants. The treatment of the plant or of the seed with the antidote can therefore be carried out essentially independently of the point of time of application of the phytotoxic chemicals. It can however be carried out also simultaneously (tank mixture). Pre-emergence treatment includes both the treatment of the cultivated area before sowing (ppi=pre plant incorporation) and the treatment of the sown area before emergence of the plants.

The applied amounts of the antidote in proportion to the amounts of herbicide depend largely on the type of application. If a field treatment is undertaken, the amounts of antidote of the formula I with respect to amounts of the phytotoxic chemical are in the ratio of 1:100 to 5:1, preferably 1:20 to 1:1. In the case of seed dressing and similar specific protective measures, much smaller amounts of antidote are required however compared with the amounts of herbicide employed for example later per hectare of cultivated area (for example about 1:3000 to 1:1000). There is as a rule only a loose connection between protective measures, such as seed dressing with an antidote of the formula I, and a possible subsequent field treatment with agricultural chemicals. Pretreated seed and plant material can later come into contact, in agriculture, horticulture and forestry, with a variety of chemicals.

The invention relates therefore also to compositions for protecting cultivated plants, which compositions contain as active substance an antidote of the formula I together with customary carriers. Compositions of this type can optionally be additionally mixed with those agricultural chemicals having an effect from which the cultivated plant is to be protected, for example they can be mixed with a herbicide.

Within the scope of the present invention, cultivated plants are all plants which produce in some form useful materials (seeds, roots, stalks, tubers, leaves, blossom, and components such as oils, sugar, starch, protein, and so forth), and which are cultivated and attented to for this purpose. These plants include for example all varieties of cereals, maize, rice, cultivated millet, soya bean, beans, peas, potatoes, vegetables, cotton, sugar beet, sugar cane, peanuts, tobacco and hops, and also ornamental plants, fruit trees as well as banana, cocoa and natural rubber plants. This list of plant types does not constitute any limitation. An antidote can as a rule be used everywhere where a cultivated plant has to be protected against the phytocoxicity of a chemical.

Compounds of the formula can be produced from the free oximes by several processes, which are shown in schematic form in the following:

(a) Carbamates

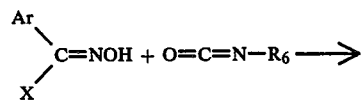

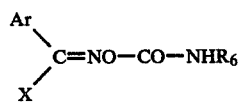

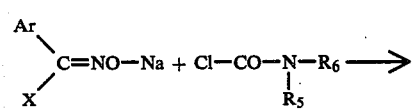

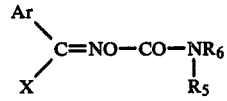

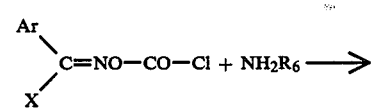

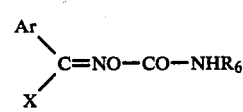

(b) (Thio) carbonates

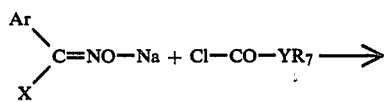

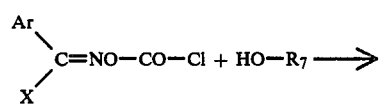

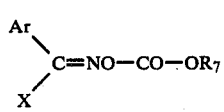

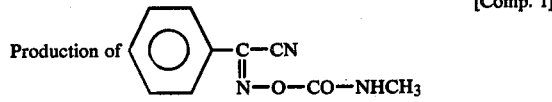

(In the preceding diagrams, Na represents sodium or another alkali metal).

Suitable for obtaining compounds of the formula I are essentially all solvents which behave inertly under the conditions of the reaction. For example, hydrocarbons, particularly however polar solvents such as acetonitrile, dioxane, cellosolve or DMF, and also ketones such as methyl ethyl ketone, acetone, and so forth. Solvents containing hydroxyl groups are excluded.

The temperatures are within the range of $-10°$ C. to about 150° C., preferably between 20° and 120° C.

As agents splitting off hydrogen halide, it is possible to use bases, such as tert. amines (triethylamine, triethylenediamine, piperidine, and so forth). Also a suspension of sodium carbonate in an anhydrous reaction medium suffices in some cases. Oximes are present in two stereoisomeric forms, the syn and arti form. By 'compounds of the formula I' are accordingly meant, within the scope of the present specification, both stereoisomeric forms, on their own or as mixtures with each other in any reciprocal mixture ratio.

The Examples which follow illustrate the production of the novel oximes of the formula I. Temperature values are given in degrees Centigrade.

EXAMPLE 1

[Comp. 1]

Production of 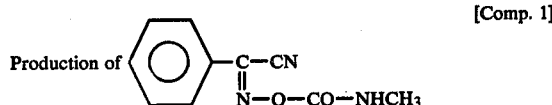

23.5 g (0.16 mol) of benzyl cyanide oxime is placed into 100 ml of acetonitrile. After 25 ml of methylisocyanate and a small, catalytically acting, amount of diazabicyclooctane have been added, the reaction mixture is heated to 50° C., and the final product precipitates after a short period of time. It is allowed to stand overnight, and is then filtered off with suction, washed with acetonitrile, and subsequently dried at 60° with hexane to yield 29.2 g (=89.8% of theory) of final product having a melting point of 172°–175° C.

EXAMPLE 2

[Comp. 53]

Production of 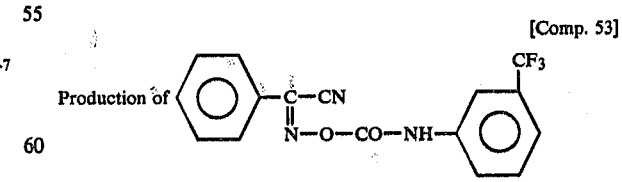

14.6 g (0.1 mol) of benzyl cyanide oxime is placed into 100 ml of acetonitrile; there are then added 18.7 g (0.1 mol) of 3-trifluoromethylphenylisocyanate and a, catalytically acting, small amount of diazabicyclooctane. The reaction commences immediately, whereupon the reaction mixture heats up to about 50°. It is stirred on a water bath for a further 4 hours; the final product which has precipitated is then filtered off with suction, washed with acetonitrile, and dried in vacuo at 50° to yield 25.5 g of final product having a melting point of 172°–173°.

EXAMPLE 3

Production of 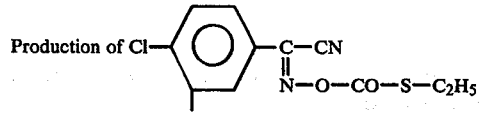  [Comp. 379]

6.3 g (0.05 mole) of chlorothioformic acid-S-ethyl ester is added dropwise to a mixture of 11.9 g (0.05 mole) of the sodium salt of 3,4-dichlorobenzyl cyanide oxime in 50 ml of acetonitrile. The reaction mixture is then heated, refluxed for 4 hours and concentrated in vacuo. Methylene chloride is added to the residue, and the mixture is stirred with active cahrcoal and filtered. The filtrate is concentrated by evaportaion to yield 11.2 g (=73.7% of theory) of the final product in the form of oil.

EXAMPLE 4

Production of 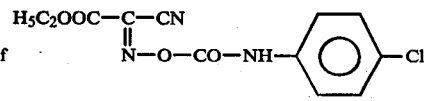  [Comp. 138]

14.2 g (0.1 mol) of cyanoacetic acid ethyl ester oxime is placed into 100 ml of acetonitrile in a flask fitted with stirrer. A solution of 15.3 g of p-chlorophenylisocyanate in 20 ml of acetonitrile is added dropwise with stirring, and the reaction mixture is stirred for 5 hours at 60°–70°. The solution is afterwards filtered hot and the filtrate is cooled in ice water. The final product which has crystallised out is filtered off, washed with acetonitrile/hexane and dried; it has a melting point of 147°–148° C.

In this manner or by one of the aforementioned methods, there can be produced the following carbamates of the formula:

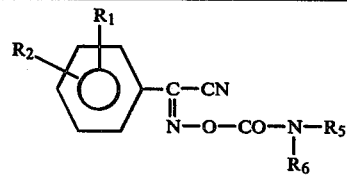

| Comp. No. | R₁ | R₂ | R₅ | R₆ | Physical constants |
|---|---|---|---|---|---|
| 1 | H | H | H | CH₃ | m.p. 172–175° |
| 2 | H | H | H | C₂H₅ | m.p. 93–96° |
| 3 | H | H | H | n-C₃H₇ | m.p. 89–91° |
| 4 | H | H | H | isoC₃H₇ | m.p. 92–94° |
| 5 | H | H | H | n-C₄H₉ | m.p. 98–101° |
| 6 | H | H | H | tert.C₄H₉ | solid |
| 7 | H | H | H | —CH₂CH₂—Cl | m.p. 138–141° |
| 8 | H | H | H | —CH₂—O—CH₃ | |
| 9 | H | H | H | ◁ | |
| 10 | H | 4-Cl | H | n-C₄H₉ | m.p. 124–126° |
| 11 | H | 4-Cl | H | —CH₂—O—CH₃ | m.p. 110–114° |
| 12 | H | 4-Cl | H | tert.C₄H₉ | m.p. 102–105° |
| 13 | H | 4-Cl | H | isoC₃H₇ | m.p. 140–144° |
| 14 | H | 4-Cl | H | CH₃ | m.p. 191–193° |
| 15 | H | 4-Cl | H | C₂H₅ | m.p. 105–108° |
| 16 | H | 4-Cl | H | nC₃H₇ | m.p. 112–113° |
| 17 | 2-Cl | 4-Cl | H | CH₃ | m.p. 152–154° |
| 18 | 2-Cl | 4-Cl | H | CH₃ | m.p. 124–128° |
| 19 | 3-Cl | 4-Cl | H | tert.C₄H₉ | solid |
| 20 | H | 4-Br | CH₃ | CH₃ | m.p. 113–115° |
| 21 | 2-Cl | 4-Cl | H | isoC₃H₇ | m.p. 92–93° |
| 22 | H | 4-Cl | CH₃ | CH₃ | m.p. 131–132° |
| 23 | 2-Cl | 4-Cl | CH₃ | CH₃ | solid |
| 24 | 4-t.C₄H₉ | H | H | CH₃ | m.p. 162–165° |
| 25 | 4-t.C₄H₉ | H | H | C₂H₅ | solid |
| 26 | 4-t.C₄H₉ | H | H | nC₃H₇ | solid |
| 27 | 4-t.C₄H₉ | H | H | tert.C₄H₉ | oil |
| 28 | H | 4-CH₃O | H | H | |
| 29 | H | 4-CH₃O | H | CH₃ | m.p. 182–184° |
| 30 | H | 4-CH₃O | H | C₂H₅ | m.p. 106–110° |
| 31 | H | 4-CH₃O | H | isoC₃H₇ | m.p. 129–131° |
| 32 | H | 4-(CH₃)₂N— | H | CH₃ | |
| 33 | H | 4-C₂H₅O | H | CH₃ | |
| 34 | H | 4-C₂H₅O | H | isoC₃H₇ | |
| 35 | H | 4-NO₂ | H | CH₃ | |
| 36 | H | 3-CF₃ | H | CH₃ | m.p. 150–151° |
| 37 | H | 3-CF₃ | H | C₂H₅ | |
| 38 | H | 3-CF₃ | H | H | |

-continued

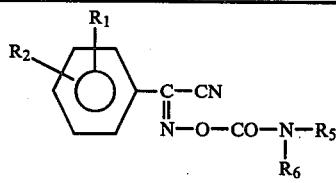

| Comp. No. | $R_1$ | $R_2$ | $R_5$ | $R_6$ | Physical constants |
|---|---|---|---|---|---|
| 39 | H | 3-$CF_3$ | $CH_3$ | $CH_3$ | |
| 40 | H | H | $C_2H_5$ | $C_2H_5$ | oil |
| 41 | H | 3-$CF_3$ | H | $nC_4H_9$ | |
| 42 | H | H | H | —$C_6H_5$ | m.p. 132–134° |
| 43 | H | H | H | —$C_6H_4Cl(4)$ | m.p. 184–186° |
| 44 | H | H | H | —$C_6H_4$—$CH_3(4)$ | m.p. 153–154° |
| 45 | H | 4-t.$C_4H_9$ | H | —$C_6H_5$ | m.p. 131–133° |
| 46 | 3-Cl | 4-Cl | H | —$C_6H_4Cl(4)$ | |
| 47 | 3-Cl | 4-Cl | H | —$C_6H_3Cl_2(3,4)$ | m.p. 210–213° |
| 48 | 3-Cl | 4-Cl | H | —$C_6H_3Cl(3)isoC_3H_7(4)$ | m.p. 172–175° |
| 49 | H | H | H | —$C_6H_4$—$CF_3(4)$ | m.p. 188–190° |
| 50 | H | H | H | —$C_6H_3Cl(3)CF_3(4)$ | m.p. 207–208° |
| 51 | H | H | H | —$C_6H_3(CF_3)_2(3,5)$ | m.p. 196–198° |
| 52 | H | H | H | —$C_6H_4$—F(4) | m.p. 159–161° |
| 53 | H | H | H | —$C_6H_4$—$CF_3(3)$ | m.p. 172–173° |
| 54 | H | 4-Cl | H | —$C_6H_4$—$CF_3(3)$ | m.p. 187–190° |
| 55 | H | 4-Cl | H | —$C_6H_4Cl(4)$ | m.p. 204–205° |
| 56 | H | 4-Cl | H | —$C_6H_3Cl_2(3,4)$ | m.p. 204–205° |
| 57 | H | 4-Cl | H | —$C_6H_3Cl(3)isoC_3H_7(4)$ | m.p. 150–151° |
| 58 | H | 4-Cl | H | —$C_6H_5$ | m.p. 148–150° |
| 59 | 2-Cl | 4-Cl | H | —$C_6H_3Cl_2(3,5)$ | solid |
| 60 | 4-t.$C_4H_9$ | H | H | —$C_6H_4Cl(4)$ | m.p. 131–133° |
| 61 | 4-t.$C_4H_9$ | H | H | —$C_6H_3Cl_2(3,4)$ | m.p. 68–71° |
| 62 | 4-t.$C_4H_9$ | H | H | —$C_6H_3(CF_3)_2(3,5)$ | m.p. 58–60° |
| 63 | H | 3-$CF_3$ | H | —$C_6H_4(CF_3)(3)$ | |
| 64 | H | 3-$CF_3$ | H | —$C_6H_4(CF_3)(4)$ | |
| 65 | H | 4-$CH_3O$ | H | —$C_6H_3Cl_2(3,4)$ | |
| 66 | H | 4-$C_2H_5O$ | H | —$C_6H_4$—$CF_3(3)$ | |
| 67 | H | 3-$CF_3$ | H | —$C_6H_5$ | m.p. 141–143° |
| 68 | H | 3-$CF_3$ | H | —iso$C_3H_7$ | m.p. 116–118° |
| 69 | 2-Cl | 4-Cl | H | —$C_6H_5$ | m.p. 163–164° |
| 70 | 2-Cl | 4-Cl | H | —$C_6H_3(CF_3)_2(3,5)$ | m.p. 110–113° |
| 71 | 2-Cl | 4-Cl | H | —$C_6H_3Cl_2(2,4)$ | m.p. 152–153° |
| 72 | 4-t.$C_4H_9$ | H | H | —$C_6H_4(CF_3)(3)$ | m.p. 136–140°; | and also following carbamates of the formula:

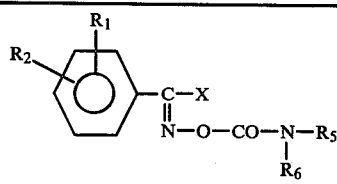

| Comp. No. | X | $R_1$ | $R_2$ | $R_5$ | $R_6$ | Physical constants |
|---|---|---|---|---|---|---|
| 73 | $CH_3$ | H | H | H | $CH_3$ | m.p. 97–99° |
| 74 | $COCH_3$ | H | H | H | $CH_3$ | |
| 75 | H | 2-Cl | 4-Cl | H | $CH_3$ | m.p. 137° |
| 76 | H | H | H | H | $CH_3$ | m.p. 92–94° |
| 77 | H | H | 4-Cl | H | $CH_3$ | m.p. 133–136° |
| 78 | H | H | 4-$(CH_3)_2N$ | H | $CH_3$ | |
| 79 | $CH_3$ | H | 4-$(C_2H_5)_2N$ | H | $CH_3$ | |
| 80 | $CH_3$ | 3-$NO_2$ | H | H | $CH_3$ | |
| 81 | H | 3-$CF_3$ | H | H | $CH_3$ | |
| 82 | —$COOC_2H_5$ | 3-$CF_3$ | H | H | $CH_3$ | |
| 83 | H | 4-$CH_3O$ | H | H | $CH_3$ | |
| 84 | $CH_3$ | 4-$CH_3O$ | H | H | $CH_3$ | |
| 85 | H | 3-$NO_2$ | H | H | $CH_3$ | |
| 86 | H | 2-$NO_2$ | H | H | $CH_3$ | |
| 87 | —$COCH_3$ | H | H | H | —$C_6H_3Cl_2(3,4)$ | |
| 88 | —$COCH_3$ | H | H | H | —$C_6H_3(CH_3)_2(2,4)$ | |
| 89 | H | H | H | H | —$C_6H_4Cl(4)$ | m.p. 145–146° |
| 90 | H | 2-Cl | 6-Cl | H | —$C_6H_4Cl(4)$ | m.p. 142–144° |
| 91 | $CH_3$ | H | H | H | —$C_6H_4Cl(4)$ | m.p. 105–106° |
| 92 | —$COCH_3$ | H | H | H | —$C_6H_4Cl(4)$ | m.p. 297–298° |

-continued

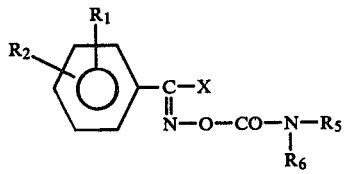

| Comp. No. | X | $R_1$ | $R_2$ | $R_5$ | $R_6$ | Physical constants |
|---|---|---|---|---|---|---|
| 93 | H | H | 4-Cl | H | $-C_6H_4Cl(4)$ | m.p. 151–152° |
| 94 | H | H | 4-Cl | H | $-C_6H_5$ | m.p. 106–109° |
| 95 | H | H | 4-Cl | H | $-C_6H_4-CH_3(3)$ | m.p. 119–121° |
| 96 | H | H | 4-Cl | H | $-C_6H_4-F(4)$ | m.p. 130–132° |
| 97 | H | H | 4-Cl | H | $-C_6H_4NO_2(4)$ | |
| 98 | $-COOC_2H_5$ | H | H | H | $CH_3$ | |
| 99 | $-COOCH_3$ | H | H | H | $CH_3$ | |
| 100 | $-COOt.C_4H_9$ | H | H | H | $CH_3$ | |
| 101 | $-COOCH_3$ | H | 4-Br | H | $CH_3$ | |
| 102 | $-COOC_2H_5$ | H | 3-$CF_3$ | H | $CH_3$ | |
| 103 | $-COOCH_3$ | H | 4-Cl | H | $-C_6H_5$ | |
| 104 | $-CONHCH_3$ | H | H | H | $CH_3$ | |
| 105 | $-CONH_2$ | H | H | H | $CH_3$ | |
| 106 | $-CONHisoC_3H_7$ | H | H | H | $CH_3$ | |
| 107 | $-CONHCH_3$ | H | 4-$CH_3O$ | H | $CH_3$ | |
| 108 | $-CONHCH_3$ | H | 4-Cl | $CH_3$ | $CH_3$ | |
| 109 | $-CONHisoC_4H_9$ | H | H | H | $CH_3$ | |
| 110 | $-CONHt.C_4H_9$ | H | 4-Cl | H | $CH_3$ | | and also following carbamates of the formula

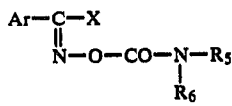

| Comp. No. | Ar | X | $R_5$ | $R_6$ | Physical constants |
|---|---|---|---|---|---|
| 111 | β-naphthyl | $-CN$ | H | $CH_3$ | m.p. 154–158° |
| 112 | β-naphthyl | $-CN$ | $C_2H_5$ | $C_2H_5$ | m.p. 162–164° |
| 113 | β-naphthyl | $-CN$ | H | $tert.C_4H_9$ | |
| 114 | β-naphthyl | $-CN$ | H | $isoC_3H_7$ | |
| 115 | β-naphthyl | $-CN$ | H | $-C_6H_4Cl(4)$ | |
| 116 | 2-furanyl | $-CN$ | H | $CH_3$ | |
| 117 | 2-furanyl | $-CN$ | H | $-CH_2-C\equiv CH$ | |
| 118 | 2-furanyl | $-CN$ | H | $-C_6H_3Cl_2(3,4)$ | |
| 119 | 2-thienyl | $-CN$ | H | $CH_3$ | |
| 120 | 2-thienyl | $-CN$ | H | $C_2H_5$ | |
| 121 | 2-thienyl | $-CH_3$ | H | $CH_3$ | |
| 122 | $(p)C_6H_5-O-C_6H_4-$ | $NO_2$ | H | $CH_3$ | |
| 123 | $(p)C_6H_5-O-C_6H_4-$ | $-COCH_3$ | H | $-C_6H_4CF_3(4)$ | |
| 124 | $H_2N-CO-$ | $-CN$ | H | $-C_6H_4Cl(3)$ | m.p. 203–204° |
| 125 | $H_2N-CO-$ | $-CN$ | H | $-C_6H_4Cl(4)$ | m.p. 201–203° |
| 126 | $H_2N-CO-$ | $-CN$ | H | $-C_6H_3Cl_2(2,5)$ | m.p. 176–177° |
| 127 | $H_2N-CO-$ | $-CN$ | H | $-C_6H_4CF_3(2)$ | m.p. 179–183° |
| 128 | $H_2N-CO-$ | $-CN$ | H | $-C_6H_4CF_3(4)$ | m.p. 170–180° |
| 129 | $H_2N-CO-$ | $-CN$ | H | $-C_6H_3Cl(3)CH_3(4)$ | m.p. 163–164° |
| 130 | $H_2N-CO-$ | $-CN$ | H | $CH_3$ | m.p. 176–177° |
| 131 | $H_2N-CO-$ | $-CN$ | H | $C_2H_5$ | m.p. 116–120° |
| 132 | $H_2N-CO-$ | $-CN$ | H | $-CH_2CH_2-Cl$ | m.p. 141–142° |
| 133 | $H_2N-CO-$ | $-CN$ | H | $-nC_3H_7$ | m.p. 113–116° |
| 134 | $H_2N-CO-$ | $-CN$ | H | $-isoC_3H_7$ | m.p. 125–126° |
| 135 | $H_2N-CO-$ | $-CN$ | H | $-nC_4H_9$ | m.p. 92–96° |
| 136 | $H_2N-CO-$ | $-CN$ | H | $-C_6H_5$ | m.p. 174–175° |
| 137 | $H_2N-CO-$ | $-CN$ | H | $-C_6H_3CF_3(3)Cl(4)$ | m.p. 182–183° |
| 138 | $C_2H_5OOC-$ | $-CN$ | H | $-C_6H_4Cl(4)$ | m.p. 147–148° |
| 139 | $C_2H_5OOC-$ | $-CN$ | H | $CH_3$ | m.p. 101–103° |
| 140 | 2-thienyl | $-CN$ | H | $-C_6H_3Cl_2(3,4)$ | oil |
| 141 | (5Cl)2-thienyl | $-CN$ | H | $CH_3$ | m.p. 186° |
| 142 | (5Cl)2-thienyl | $-CN$ | H | $-C_6H_4Cl(4)$ | m.p. 186° |
| 143 | (5Cl)2-thienyl | $-CN$ | H | $-C_6H_3Cl(4)CF_3(3)$ | m.p. 184°; | and also following carbamates of the formula:

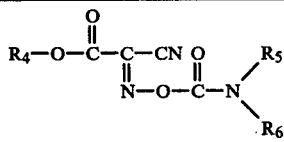

| Comp No. | R₄ | R₅ | R₆ | Physical constants |
|---|---|---|---|---|
| 144 | CH₃O— | H | C₆H₃CF₃(3)Cl(4) | m.p. 162–163° |
| 145 | CH₃O— | H | C₆H₄CF₃(3) | m.p. 147–148° |
| 146 | CH₃O— | H | C₆H₅ | m.p. 149–150° |
| 147 | CH₃O— | H | C₆H₄NO₂(3) | m.p. 166–167° |
| 148 | CH₃O— | H | C₆H₄Cl(4) | m.p. 162–163° |
| 149 | CH₃O— | H | C₆H₄Cl(4) | m.p. 157–158° |
| 150 | CH₃O— | H | C₆H₄Cl(2) | m.p. 136–138° |
| 151 | CH₃O— | H | C₆H₄CF₃(4) | m.p. 127–128° |
| 152 | CH₃O— | H | C₆H₄(OC₄H₉(i))(4) | m.p. 139–140° |
| 153 | CH₃O— | H | C₆H₃Cl₂(3,4) | m.p. 162–163° decomp. |
| 154 | CH₃O— | H | C₆H₃Cl(3)Br(4) | m.p. 170–171° |
| 155 | CH₃O— | H | C₆H₃Cl₂(2,5) | m.p. 164–165° |
| 156 | CH₃O— | H | C₆H₃CH₃(2)Cl(3) | m.p. 118–120° |
| 157 | CH₃O— | H | C₆H₃CH₃(2)Cl(4) | m.p. 119–120° |
| 158 | CH₃O— | H | C₆H₃Br(2)CH₃(4) | m.p. 134–135° |
| 159 | CH₃O— | H | C₆H₃(CH₃)₂(2,4) | m.p. 115–117° |
| 160 | CH₃O— | H | C₆H₃Cl(2)NO₂(4) | m.p. 165–166° decomp. |
| 161 | CH₃O— | H | C₆H₃Cl₂(2,4) | m.p. 143–145° |
| 162 | CH₃O— | H | —CH₃ | m.p. 122–123° |
| 163 | CH₃O— | H | —CH₂CH₂Cl | m.p. 72–74° |
| 164 | C₂H₅—O | H | —C₆H₅ | m.p. 130–132° |
| 165 | C₂H₅—O | H | —C₆H₄Cl(2) | m.p. 81–82° |
| 166 | C₂H₅—O | H | —C₆H₄Cl(3) | m.p. 139–141° |
| 167 | C₂H₅—O | H | —C₆H₄Cl(4) | m.p. 156–157° |
| 168 | C₂H₅—O | H | —C₆H₄CF₃(3) | m.p. 117–119° |
| 169 | C₂H₅—O | H | —C₆H₄CF₃(4) | m.p. 136–137° |
| 170 | C₂H₅—O | H | —C₆H₄NO₂(3) | m.p. 145–147° |
| 171 | C₂H₅—O | H | —C₆H₄CH₃(4) | m.p. 121–122° |
| 172 | C₂H₅—O | H | —C₆H₄(O—C₄H₉(i))(4) | m.p. 127–128° |
| 173 | C₂H₅—O | H | —C₆H₃Cl₂(3,4) | m.p. 160–161° |
| 174 | C₂H₅—O | H | —C₆H₃Cl₂(2,5) | m.p. 136–137° |
| 175 | C₂H₅—O | H | —C₆H₃CF₃(3)Cl(4) | m.p. 141–142° |
| 176 | C₂H₅—O | H | —C₆H₃Cl(2)NO₂(4) | m.p. 133–134° |
| 177 | C₂H₅—O | H | —C₆H₃(CF₃)₂(3,5) | m.p. 155–157° |
| 178 | C₂H₅—O | H | —C₆H₃CH₃(2)Cl(4) | m.p. 90–91° |
| 179 | C₂H₅—O | H | —C₆H₂Cl₃(2,4,5) | m.p. 137–139° |
| 180 | C₂H₅—O | H | —CH₃ | m.p. 104–106° |
| 181 | C₂H₅—O | H | —CH₂Cl₂ | m.p. 73–75° |
| 182 | (s)C₄H₉—O | H | —C₆H₄Cl(4) | m.p. 128°–130° |
| 183 | (s)C₄H₉—O | H | —C₆H₄CF₃(3) | m.p. 93°–95° |
| 184 | (s)C₄H₉—O | H | —C₆H₄CF₃(4) | m.p. 109–110° |
| 185 | (s)C₄H₉—O | H | —C₆H₃Cl₂(3,4) | m.p. 140–141° |
| 186 | (s)C₄H₉—O | H | —C₆H₃Cl₂(2,5) | m.p. 100–101° |
| 187 | (s)C₄H₉—O | H | —C₆H₃CF₃(3)Cl(4) | m.p. 126–127° |
| 188 | (s)C₄H₉—O | H | —CH₃ | m.p. 80–81° |
| 189 | (s)C₄H₉—O | H | —CH₂CH₂Cl | m.p. 57–59° |
| 190 | CH₂=CH—CH₂—O | H | C₆H₅ | m.p. 103–105° |
| 191 | CH₂=CH—CH₂—O | H | C₆H₄Cl(3) | m.p. 118–120° |
| 192 | CH₂=CH—CH₂—O | H | C₆H₄Cl(4) | m.p. 131–132° |
| 193 | CH₂=CH—CH₂—O | H | C₆H₄CF₃(3) | m.p. 106–107° |
| 194 | CH₂=CH—CH₂—O | H | C₆H₄CF₃(4) | m.p. 121–123° |
| 195 | CH₂=CH—CH₂—O | H | C₆H₃Cl₂(3,4) | m.p. 126–127° |
| 196 | CH₂=CH—CH₂—O | H | C₆H₃Cl₂(2,5) | m.p. 130–131° |
| 197 | CH₂=CH—CH₂—O | H | C₆H₂Cl₃(2,4,5) | m.p. 124–126° |
| 198 | CH₂=CH—CH₂—O | H | —CH₂CH₂Cl | m.p. 61–63° |
| 199 | ⟨H⟩—O— | H | —C₆H₄Cl(4) | m.p. 141–142° |
| 200 | ⟨H⟩—O— | H | —C₆H₄CF₃(3) | m.p. 94–96° |
| 201 | ⟨H⟩—O— | H | —C₆H₄Cl(4) | m.p. 162–163° |
| 202 | ⟨H⟩—O— | H | —C₆H₃CF₃(3Cl(4) | m.p. 131–132° |

-continued

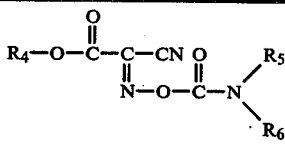

| Comp. No. | R₄ | R₅ | R₆ | Physical constants |
|---|---|---|---|---|
| 203 | C₆H₅—O— | H | —C₆H₂Cl₃(2,4,5) | m.p. 124–126° |
| 204 | C₆H₅—O— | H | —CH₃ | m.p. 99–101° |
| 205 | C₆H₅—CH=CH—CH₂O— | H | —C₆H₄Cl(3) | m.p. 136° (decomp.) |
| 206 | C₆H₅—CH=CH—CH₂O— | H | —C₆H₃Cl₂(3,4) | m.p. 138° (decomp.) |
| 207 | C₆H₅—CH=CH—CH₂O— | H | —C₆H₂Cl₃(2,4,5) | m.p. 161° (decomp.) |
| 207a | CH₃O | CH₃ | —CH₃ | m.p. 105–106° |
| 208 | CH₃O | H | C₆H₃Cl₂(3,5) | m.p. 156° (decomp.) |
| 209 | C₆H₅—O— | H | C₆H₃Cl₂(3,5) | m.p. 107–108° |
| 210 | C₆H₅—O— | H | C₆H₃Cl₂(3,4) | m.p. 162–163° |
| 211 | CH₃O— | H | C₆H₃Cl₂(3,4) | m.p. 162–163°; | and also following carbamates of the formula

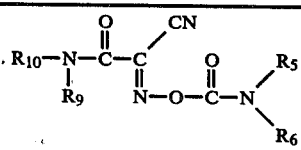

| Comp. No. | R₅ | R₆ | R₉ | R₁₀ | Physical constants |
|---|---|---|---|---|---|
| 212 | H | C₆H₃Cl₂(3,4) | —CH₃ | —CH₃ | m.p. 153–154° |
| 213 | H | C₆H₃CF₃(3)Cl(4) | —CH₃ | —CH₃ | m.p. 154–156° |
| 214 | H | C₆H₅ | | C₆H₁₁ | m.p. 143–144° |
| 215 | H | C₆H₄Cl(2) | | C₆H₁₁ | m.p. 120–123° |
| 216 | H | C₆H₄Cl(4) | | C₆H₁₁ | m.p. 142–144° |
| 217 | H | C₆H₄CF₃(4) | | C₆H₁₁ | m.p. 160–162° |

-continued

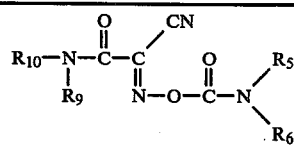

| Comp. No. | R₅ | R₆ | R₉ | R₁₀ | Physical constants |
|---|---|---|---|---|---|
| 218 | H | C₆H₃Cl₂(3,4) | | ⬡—H | m.p. 153–154° |
| 219 | H | C₆H₄CH₃(4) | | ⬡—H | m.p. 133–135° |
| 220 | H | C₆H₃CF₃(3)Cl(4) | | ⬡—H | m.p. 140° (decomp.) |
| 221 | H | C₆H₃Cl(2)NO₂(4) | | ⬡—H | m.p. 165° (decomp.) |
| 222 | H | C₆H₂Cl₃(2,4,5) | | ⬡—H | m.p. 143–145° |
| 223 | H | —CH₃ | | ⬡—H | m.p. 113° (decomp.) |
| 224 | H | C₆H₅ | | cyclopropyl | m.p. 124–125° |
| 225 | | C₆H₄Cl(4) | | cyclopropyl | m.p. 125–127° |
| 226 | H | C₆H₃Cl₂(3,4) | | cyclopropyl | m.p. 155–157° |
| 227 | H | C₆H₃CF₃(3)Cl(4) | | cyclopropyl | m.p. 145° (decomp.) |
| 228 | H | —CH₃ | | cyclopropyl | m.p. 90° (decomp.) |
| 229 | H | C₃H₇ | CH₃ | CH₃ | m.p. 46–50° |
| 230 | H | CH(CH₃)₂ | CH₃ | CH₃ | m.p. 62–66° |
| 231 | H | C₄H₉ | CH₃ | CH₃ | oil |
| 232 | H | C₂H₅ | CH₃ | CH₃ | m.p. 90° |
| 233 | H | CH(CH₃)₂ | H | H | m.p. 206–207° |
| 234 | H | CH₃ | CH₃ | CH₃ | m.p. 72–76° |
| 235 | H | CH₂CH₂Cl | CH₃ | CH₃ | m.p. 99–101° |
| 236 | H | C₆H₄Cl(3) | | 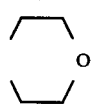 | m.p. 159–161° |

-continued

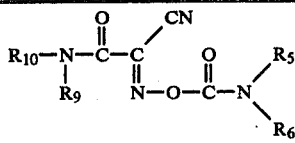

| Comp. No. | R5 | R6 | R9 | R10 | Physical constants |
|---|---|---|---|---|---|
| 237 | H | $C_6H_4CF_3(3)$ | | (tetrahydropyran) | m.p. 130–132° |
| 238 | H | $C_6H_3CF_3(3)Cl(4)$ | | (tetrahydropyran) | m.p. 176–178° |
| 239 | H | $C_6H_5$ | H | $-C_6H_4CF_3(3)$ | m.p. 163° (decomp.) |
| 240 | H | $C_5H_4Cl(4)$ | H | $-C_6H_4CF_3(3)$ | m.p. 180° (decomp.) |
| 241 | H | $C_6H_3Cl_2(3,4)$ | H | $-C_6H_4CF_3(3)$ | m.p. 161° (decomp.) |
| 242 | H | $C_6H_3CF_3(3)Cl(4)$ | H | $-C_6H_4CF_3(3)$ | m.p. 169° (decomp.) |
| 243 | H | $C_6H_5$ | H | $-C_6H_3Cl_2(2,4)$ | m.p. 179° (decomp.) |
| 244 | H | $C_6H_4Cl(3)$ | H | $-C_6H_3Cl_2(2,4)$ | m.p. 154° (decomp.) |
| 245 | H | $C_6H_4Cl(4)$ | H | $-C_6H_3Cl_2(2,4)$ | m.p. 172° (decomp.) |
| 246 | H | $C_6H_4CF_3(3)$ | H | $-C_6H_3Cl_2(2,4)$ | m.p. 165° (decomp.) |
| 247 | H | $C_6H_4CH_3(3)$ | H | $-C_6H_3Cl_2(2,4)$ | m.p. 152° (decomp.) |
| 248 | H | $C_6H_3Cl_2(3,4)$ | H | $-C_6H_3Cl_2(2,4)$ | m.p. 176° (decomp.) |
| 249 | H | $C_6H_3Cl_2(2,5)$ | H | $-C_6H_3Cl_2(2,4)$ | m.p. 185° (decomp.) |
| 250 | H | $C_6H_3CF_3(3)Cl(4)$ | H | $-C_6H_3Cl_2(2,4)$ | m.p. 162° (decomp.) |
| 251 | H | $C_6H_3CH_3(2)Cl(4)$ | H | $-C_6H_3Cl_2(2,4)$ | m.p. 154° (decomp.) |
| 252 | H | $C_6H_3CH_3(2)Cl(3)$ | H | $-C_6H_3Cl_2(2,4)$ | m.p. 140° (decomp.) |
| 253 | H | $C_6H_3Cl_2(2,4)$ | H | $-C_6H_3Cl_2(2,4)$ | m.p. 172° (decomp.) |
| 254 | H | $C_6H_9Cl(3)$ | H | $-C_6H_3(CF_3)_2(3,5)$ | m.p. 165° (decomp.) |
| 255 | H | $C_6H_4Cl(4)$ | H | $-C_6H_3(CF_3)_2(3,5)$ | m.p. 179° (decomp.) |
| 256 | H | $C_6H_4CF_3(4)$ | H | $-C_6H_3(CF_3)_2(3,5)$ | m.p. 188° (decomp.) |
| 257 | H | $C_6H_4Cl(4)$ | H | $-C_6H_3Cl(2)NO_2(4)$ | m.p. 187° (decomp.) |
| 258 | H | $C_6H_4CF_3(4)$ | H | $-C_6H_3Cl(2)NO_2(4)$ | m.p. 198° (decomp.) |
| 259 | H | $C_6H_3Cl_2(3,4)$ | H | $-C_6H_3Cl(2)NO_2(4)$ | m.p. 198° (decomp.) |
| 260 | H | $C_6H_3Cl(2)NO_2(4)$ | H | $-C_6H_3Cl(2)NO_2(4)$ | m.p. 185° (decomp.) |
| 261 | $-CH_3$ | $-CH_3$ | | (cyclohexyl) | m.p. 104–105° |
| 262 | $-CH_3$ | $-CH_3$ | H | $-C_6H_3CH_3(2)Cl(3)$ | m.p. 164° (decomp.) |
| 263 | $-CH_3$ | $-CH_3$ | H | $-C_6H_4CF_3(3)$ | m.p. 115–117° |
| 264 | $-CH_3$ | $-CH_3$ | H | $-C_6H_3Cl_2(2,5)$ | m.p. 162–164° |
| 265 | $-CH_3$ | $-CH_3$ | | (cyclopropyl) | m.p. 71–72° |
| 266 | H | $C_6H_3Cl_2(2,5)$ | H | 2,5-dibromo-4-methylphenyl | m.p. 120° (decomp.) |
| 267 | H | $C_6H_4Cl(3)$ | H | $CH_2CH=CH_2$ | m.p. 154° (decomp.) |
| 268 | H | $C_6H_3Cl(3)Cl(4)$ | H | $CH_2CH=CH_2$ | m.p. 175° (decomp.) |
| 269 | H | $C_6H_3Cl(3)CF_3(4)$ | H | $CH_2CH=CH_2$ | m.p. 139° (decomp.) |
| 270 | H | $C_6H_4Cl(4)$ | H | $CH_2CH=CH_2$ | m.p. 170° (decomp.) |
| 271 | H | $C_6H_3Cl_2(3,4)$ | H | $CH_2CH=CH_2$ | m.p. 164° (decomp.) |
| 272 | H | $-CH_3$ | H | $CH_2CH=CH_2$ | m.p. 111–113° |
| 273 | H | $CH(CH_3)_2$ | H | $C_2H_5$ | m.p. 103–105° |
| 274 | H | $C_3H_7$ | H | $C_2H_5$ | m.p. 78–90° |
| 275 | H | $C_4H_9$ | H | $C_2H_5$ | m.p. 70.5–74° |
| 276 | H | $C_3H_7$ | H | $CH_3$ | m.p. 67–70° |
| 277 | H | $CH(CH_3)_2$ | H | $CH_3$ | m.p. 116–118.5° |
| 278 | H | $C_4H_9$ | H | $CH_3$ | m.p. 107–109° |
| 279 | H | $CH_2-CH_2-Cl$ | H | $CH_3$ | m.p. 105–106° |
| 280 | H | $C_6H_4Cl(4)$ | H | $nC_3H_5$ | m.p. 177–178° |
| 281 | H | $C_6H_3Cl_2(3,4)$ | H | $nC_3H_5$ | m.p. 180° (decomp.) |

-continued

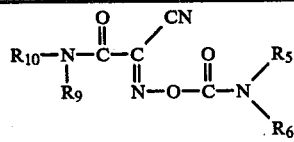

| Comp. No. | R5 | R6 | R9 | R10 | Physical constants |
|---|---|---|---|---|---|
| 282 | H | C6H3Cl(3)CH3(4) | H | nC3H5 | m.p. 166–167° |
| 283 | H | —CH3 | H | nC3H5 | m.p. 124–126° |
| 284 | H | C6H4Cl(3) | H | C6H3Cl2(3,5) | m.p. 190° (decomp.) |
| 285 | H | C6H3CF3(3)Cl(4) | H | C6H3Cl2(3,5) | oil |
| 286 | H | C6H3Cl2(3,4) | H | C6H3Cl2(3,5) | m.p. 173° (decomp.) |
| 287 | H | C6H3Cl(3)CF3(4) | H | C6H3Cl2(3,5) | m.p. 182° (decomp.) |
| 288 | H | C6H4CF3(4) | H | C6H3Cl2(3,5) | m.p. 169° (decomp.) |
| 289 | H | CH3CH2Cl | H | H | m.p. 141–142° |
| 290 | H | —CH3 | H | CH3 | m.p. 167–168°; | and also the following carbamates of the formula

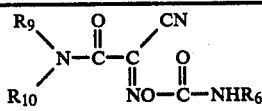

| Comp. No. | R6 | R9 | R10 | Physical constants |
|---|---|---|---|---|
| 291 | C6H4Cl(3) | H | CH3 | m.p. 177–178° |
| 292 | C6H4Cl(3) | H | C2H5 | m.p. 166–167° |
| 293 | C6H4Cl(3) | H | H | m.p. 203° (decomp.) |
| 294 | C6H4Cl(3) | CH3 | CH3 | m.p. 125–126° |
| 295 | C6H4Cl(4) | H | CH3 | m.p. 198–200° |
| 296 | C6H4Cl(4) | H | H | m.p. 203° (decomp.) |
| 297 | C6H4Cl(4) | H | C2H5 | m.p. 180° (decomp.) |
| 298 | C6H4Cl(4) | CH3 | CH3 | m.p. 161–162° |
| 299 | C6H3CH3(4)Cl(3) | H | CH3 | m.p. 180° (decomp.) |
| 300 | C6H3CH3(4)Cl(3) | CH3 | CH3 | m.p. 144–146° |
| 301 | C6H3CH3(4)Cl(3) | H | C2H5 | m.p. 163–163.5° |
| 302 | C6H3CH3(4)Cl(3) | H | C4H9(n) | m.p. 142–145° |
| 303 | C6H3CH3(4)Cl(3) | H | H | m.p. 163–166° |
| 304 | C6H3Cl2(3,4) | H | CH3 | m.p. 195° (decomp.) |
| 305 | C6H3Cl2(3,4) | H | C2H5 | m.p. 175.5° (decomp.) |
| 306 | C6H3Cl2(3,4) | H | C4H9 | m.p. 167.5–170° |
| 307 | C6H3Cl2(3,4) | H | H | m.p. 192–193° |
| 308 | C6H3CF3(3)Cl(4) | H | CH3 | m.p. 198° (decomp.) |
| 309 | C6H3CF3(3)Cl(4) | H | C2H5 | m.p. 185° (decomp.) |
| 310 | C6H3CF3(3)Cl(4) | H | H | m.p. 183° (decomp.) |
| 311 | C6H3CF3(3)Cl(4) | H | C3H7(n) | m.p. 172° (decomp.) |
| 312 | C6H3CF3(3)Cl(4) | H | C4H9(n) | m.p. 174–177° |
| 313 | C6H3Cl(3)CF3(4) | CH3 | CH3 | m.p. 156–158° |
| 314 | C6H3Cl(3)CF3(4) | H | H | m.p. 191° (decomp.) |
| 315 | C6H3Cl(3)CF3(4) | H | CH3 | m.p. 183–185° |
| 316 | C6H3Cl(3)CF3(4) | H | C2H5 | m.p. 167–169° |
| 317 | C6H3Cl(3)CF3(4) | H | C4H9(n) | m.p. 149–150° |
| 318 | C6H4CF3(2) | H | H | m.p. 183° (decomp.) |
| 319 | C6H4CF3(2) | H | CH3 | m.p. 193° (decomp.) |
| 320 | C6H4CF3(4) | H | H | m.p. 180° (decomp.) |
| 321 | C6H4CF3(4) | H | CH3 | m.p. 189° (decomp.) |
| 322 | C6H4CF3(4) | CH3 | CH3 | m.p. 134–135° |
| 323 | C6H4Cl(3) | H | C3H7(n) | m.p. 155–157° |
| 324 | C6H4Cl(4) | H | C3H7(n) | m.p. 170° (decomp.) |
| 325 | C6H4Cl(4) | H | C4H9(n) | m.p. 170–174° |
| 326 | C6H3Cl2(3,5) | H | H | m.p. 200° (decomp.) |
| 327 | C6H3Cl2(3,5) | H | C2H5 | m.p. 159° (decomp.) |
| 328 | C6H3Cl2(3,5) | H | CH3 | m.p. 194° (decomp.) |
| 329 | C6H4CF3(3) | H | CH3 | m.p. 190° (decomp.) |
| 330 | C6H4CF3(3) | CH3 | CH3 | m.p. 109–110° |
| 331 | C6H5 | H | H | m.p. 175° (decomp.) |
| 332 | C6H5 | H | CH3 | m.p. 162–163.5° |
| 333 | C6H3Cl2(2,3) | H | H | m.p. 156° (decomp.) |
| 334 | CH3 | H | H | m.p. 177° (decomp.) |
| 335 | CH2CH3 | H | H | m.p. 116–120° |
| 336 | CH3 | H | C2H5 | m.p. 119.5–124° |
| 337 | C3H7(n) | H | H | m.p. 113–116° |
| 338 | C6H3Cl(3)CH3(4) | H | H | m.p. 163–164° |
| 339 | C6H3CH3(4)Cl(3) | H | CONH2 | m.p. 197° (decomp.) |
| 340 | C6H3Cl2(3,4) | H | CONH2 | m.p. 205° (decomp.) |

-continued

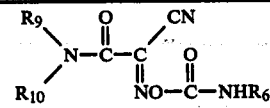

| Comp. No. | R6 | R9 | R10 | Physical constants |
|---|---|---|---|---|
| 341 | C6H3CF3(3)Cl(4) | H | CONH2 | m.p. 200° (decomp.) |
| 342 | C6H4Cl(3) | H | CONH2 | m.p. 206° (decomp.) |
| 343 | C6H3Cl(3)CH3(4) | H | CONH2 | m.p. 197° (decomp.) |
| 344 | C6H3Cl2(3,5) | H | CONH2 | m.p. 197° (decomp.) |
| 345 | C6H4CF3(3) | H | CONH2 | m.p. 208° (decomp.) |
| 346 | C6H5 | H | CONH2 | m.p. 214–215° |
| 347 | C6H3Cl2(2,3) | H | CONH2 | m.p. 203° (decomp.) |
| 348 | CH3 | H | CONH2 | m.p. 216° (decomp.); | and also following carbamates of the formula:

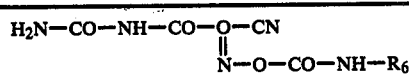

| Comp. No. | R6 | Physical constants |
|---|---|---|
| 349 | C4H9(n) | m.p. 131° (decomp.) |
| 350 | C3H7(n) | m.p. 133° (decomp.) |
| 351 | C3H7(iso) | m.p. 207° (decomp.) |
| 352 | —CH2—CH2—Cl | m.p. 140–145° (decomp.) |
| 353 | C3H7(iso) | m.p. 207° (decomp.). |

The following (thio)carbonates are produced according to Example 3 or by one of the methods given in the foregoing:

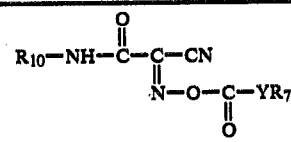

| Comp. No. | YR7 | R10 | Physical constants |
|---|---|---|---|
| 354 | OC6H5 | H | m.p. 149° (decomp.) |
| 355 | OCH3 | H | m.p. 170° (decomp.) |
| 356 | OC3H7(iso) | H | m.p. 171–173° |
| 357 | OCH3 | CH3 | m.p. 97–98.5° |
| 358 | OC4H9(n) | H | m.p. 165–167° |
| 359 | OC3H7(iso) | CH3 | m.p. 109–110° |
| 360 | O(CH2)3CH3 | CH3 | m.p. 75–76° |
| 361 | OCH3 | H | m.p. 120–121° |
| 362 | OCH3 | CH3 | m.p. 73–74° |
| 363 | OC6H5 | —CONH2 | m.p. 168° (decomp.) |

-continued

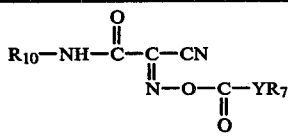

| Comp. No. | YR$_7$ | R$_{10}$ | Physical constants |
|---|---|---|---|
| 364 | OCH$_3$ | —CONH$_2$ | m.p. 171–172° |
| 365 | SC$_2$H$_5$ | H | m.p. 124–125 |
| 366 | OC$_4$H$_9$(n) | —CONH$_2$ | m.p. 173° (decomp.) |
| 367 | OC$_3$H$_7$(iso) | —CONH$_2$ | m.p. 173° (decomp.) |
| 368 | SC$_2$H$_5$ | —CONH$_2$ | m.p. 179° (decomp.) |
| 369 | SC$_2$H$_5$ | CH$_3$ | m.p. 76–78°. |

In the manner described in Example 3 or by one of the methods described in the foregoing, there can be produced following carbonates of the formula:

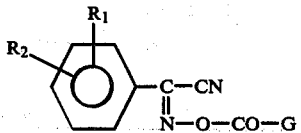

| Comp. No. | R$_1$ | R$_2$ | G | Physical constants |
|---|---|---|---|---|
| 370 | H | H | —O—C$_6$H$_5$ | m.p. 105–108° |
| 371 | H | H | —O—isoC$_3$H$_7$ | m.p. 108–110° |
| 372 | H | H | —O—CH$_2$CH$_2$OCH$_3$ | oil |
| 373 | H | H | —O—CH$_3$ | m.p. 108–110° |
| 374 | H | H | —O—CH$_2$—CCl$_3$ | solid |
| 375 | H | H | —O—C$_6$H$_4$NO$_2$(4) | solid |
| 376 | H | H | —S—nC$_4$H$_9$ |  |
| 377 | H | H | —O—tert.C$_4$H$_9$ | m.p. 85–86° |
| 378 | H | H | —S—C$_2$H$_5$ | m.p. 59–62° |
| 379 | 3-Cl | 4-Cl | —S—C$_2$H$_5$ | oil |

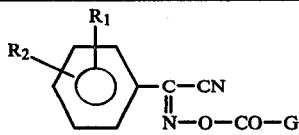

| Comp. No. | R$_1$ | R$_2$ | G | Physical constants |
|---|---|---|---|---|
| 380 | H | 4-Cl | —S—C$_2$H$_5$ | oil |
| 381 | 2-Cl | 4-Cl | —S—C$_2$H$_5$ | oil |
| 382 | H | 4-CH$_3$ | —S—C$_2$H$_5$ | oil |
| 383 | H | H | —O—C$_6$H$_4$Cl(4) |  |
| 384 | H | 4-Cl | —O—sec.C$_4$H$_9$ |  |
| 385 | H | 3-CF$_3$ | —O—CH$_3$ |  |
| 386 | H | 3-CF$_3$ | —O—C$_6$H$_5$ |  |
| 387 | H | 3-CF$_3$ | —S—C$_2$H$_5$ |  |
| 388 | H | 3-CF$_3$ | —S—CH$_3$ |  |
| 389 | H | 4-Br | —S—C$_2$H$_5$ |  |
| 390 | H | 4-CH$_3$O | —O—C$_6$H$_4$—OCH$_3$(4) | oil |
| 391 | H | 4-CH$_3$O | —O—C$_6$H$_4$Cl(4) | viscous |
| 392 | H | 4-C$_2$H$_5$O | —O—isoC$_3$H$_7$ | oil, | and also the following carbonates of the formula:

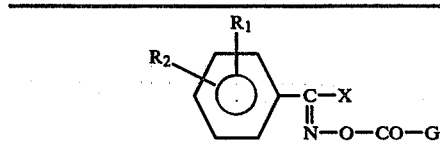

| Comp. No. | R$_1$ | R$_2$ | X | G | Physical constants |
|---|---|---|---|---|---|
| 393 | H | 4-(CH$_3$)$_2$N | H | —OC$_2$H$_5$ | oil |
| 394 | H | 4-CH$_3$O | H | —S—C$_2$H$_5$ | oil |
| 395 | H | 4-Cl | —COOCH$_3$ | —OCH$_3$ | oil | and the following compounds:

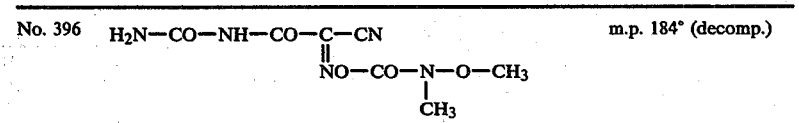

No. 396   H$_2$N—CO—NH—CO—C—CN with NO—CO—N(CH$_3$)—O—CH$_3$   m.p. 184° (decomp.)

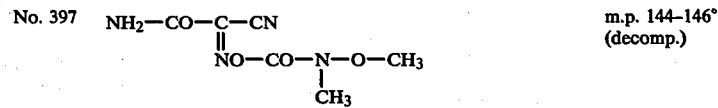

No. 397   NH$_2$—CO—C(CN)=NO—CO—N(CH$_3$)—O—CH$_3$   m.p. 144–146° (decomp.)

No. 398   H$_5$C$_6$—C(Cl)=NO—CO—NHCH$_3$   oil
No. 399   H$_5$C$_2$O—CO—C(CN).NO—CO—SC$_2$H$_5$   oil
No. 400   H$_5$C$_2$O—CO—C(CH$_3$)=NO—CO—NHCH$_3$   m.p. 83–85°

No. 401   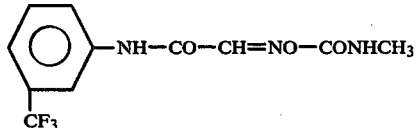   m.p. 126° (decomp.)

(3-CF$_3$-C$_6$H$_4$)—NH—CO—CH=NO—CONHCH$_3$

No. 402   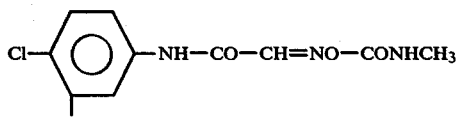   m.p. 145° (decomp.)

(Cl, CF$_3$-C$_6$H$_3$)—NH—CO—CH=NO—CONHCH$_3$

| | |
|---|---|
| No. 403 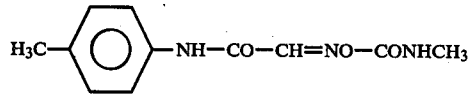 | m.p. 170° (decomp.). |

As already mentioned, various methods and techniques are suitable for application of the compounds of the formula I for the protection of cultivated plants against agricultural chemicals:

1. Seed dressing (a) Dressing of the seed with an active substance formulated as a wettable powder by shaking in a vessel until there exists a uniform distribution over the surface of the seeds (dry dressing). The amount of active substance of the formula I used for this purpose is about 10 to 500 g (40 g to 2 kg of wettable powder) per 100 kg of seed, (b) Dressing of the seed with an emulsion concentrate of the active substance of the formula I using method (a) (wet dressing).

(c) Dressing by immersion of the seed in a liquor containing 50–3200 ppm of active substance of the formula I for 1–72 hours and, optionally, subsequent drying of the seed (immersion dressing).

The dressing of the seed or the treatment of the germinated seedlings are naturally the preferred methods of application because the treatment with the active substance is directed completely at the target crop. There is used as a rule 10 g to 500 g, preferably 50 to 250 g, of active substance per 100 kg of seed, it being possible, depending on the method used, which method enables also the addition of other active substances or micronutrients to be made, to deviate either upwards or downwards from the given limiting concentrations (repeat dressings).

2. Application as a tank mixture

A liquid preparation of a mixture of antidote and herbicide (reciprocal quantitative ratio between 1:20 and 5:1 is used, the applied amount of herbicide being 0.1 to 6 kg per hectare. A tank mixture of this type is preferably applied before or immediately after sowing, or is worked into the unsown soil to a depth of 5–10 cm.

(3) Application into the seed furrow

The antidote is introduced, as an emulsion concentrate, wettable powder or granulate, into the open sown seed furrow and, after covering of the seed furrow in the normal manner, the herbicide is applied using the pre-emergence process.

Essentially, the antidote can therefore be applied before, together with, or after the herbicide, and its aplication to the seeds or to the field can be effected either before or after sowing, or in certain cases also after germination of the seed.

(4) Controlled release of active substance

The active substance in solution is absorbed onto mineral granulate carriers or onto polymerised granules (urea/formaldehyde), and the material is allowed to dry. It is possible if desired to apply a coating (coated granules), which enables the active substance to be released in controlled amounts over a specific period of time.

The term "seed" within the meaning of the foregoing is not limited to kernels (of cereals, etc.) but encompasses all propagative organs of cultivated plants. By the term "propagative organs" are meant all generative plant parts which can be used for the propagation of the cultivated plants. These parts include kernels, roots, fruits, tubers, rhizomes and stalks, and also emerged plants and seedlings which are intended for transplanting.

It is naturally possible to employ also all other known methods of applying active substances. Examples in this connection are given later in the text.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

The compounds of the formula I can be in the following forms for application (the weight-percentage figures in brackets signify advantageous amounts of active substance):

solid preparations:
  dusts and scattering agents (up to 10%), and granulates [coated granules, impregnated granules and homogeneous granules] (1 to 80%);

liquid preparations:
  (a) water-dispersible concentrates of active substance: wettable powders and pastes (25 to 90% in the commercial packing, 0.01 to 15% ready-for-use solutions); emulsion concentrates and solution concentrates (10 to 50%; 0.01 to 15% in ready-for-use solutions);
  (b) solutions (0.1 to 20%) and aerosols.

The active substances of the formula I of the present invention can be formulated for example as follows.

Dust:

The following substances are used to produce (a) a 5% dust and (b) a 2% dust:
  (a) 5 parts of active substance, and 95 parts of talcum,
  (b) 2 parts of active substance, 1 part of highly dispersed silicic acid, and 97 parts of talcum.

The active substances are mixed and ground with the carriers, and in this form they can be applied by dusting.

Granulate:

The following substances are used to produce a 5% granulate:
  5 parts of active substance,
  0.25 part of epichlorohydrin,
  0.25 part of cetyl polyglycol ether,
  3.50 parts of polyethylene glycol, and
  91 parts of kaolin (particle size 0.3–0.8 mm).

The active substance is mixed with epichlorohydrin and dissolved in 6 parts of acetone, and the polyethylene glycol and cetyl polyglycol ether are then added. The solution thus obtained is sprayed onto kaolin, and the acetone is subsequently evaporated off in vacuo.

Wettable powder:

The following constituents are used to produce (a) a 70% wettable powder, (b) a 40% wettable powder, (c) and (d) a 25% wettable powder, and (e) a 10% wettable powder:

(a)
  70 parts of active substance,
  5 parts of sodium dibutylnaphthylsulfonate,
  3 parts of naphthalenesulionic acid/phenolsulfonic acid/formaldehyde condensate 3:2:1,
  10 parts of kaolin, and
  12 parts of Champagne chalk;
(b)
  40 parts of active substance,
  5 parts of sodium lignin sulfonate,
  1 part of sodium dibutylnaphthalenesulfonate,
  54 parts of silicic acid;
(c)
  25 parts of active substance,
  4.5 parts of calcium lignin sulfonate,
  1.9 parts of Champagne chalk/hydroxyethyl cellulose mixture (1:1),
  1.5 parts of sodium dibutylnaphthalenesulfonate,
  19.5 parts of silicic acid,
  19.5 parts of Champagne chalk, and
  28.1 parts of kaolin;
(d)
  25 parts of active substance,
  2.5 parts of isooctylphenoxy-polyoxyethyleneethanol,
  1.7 parts of Champagne chalk/hydroxyethylcellulose mixture (1:1),
  8.3 parts of sodium aluminium silicate,
  16.5 parts of kieselgur, and
  46 parts of kaolin, and
(e)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give suspensions of the desired concentration.

Emulsifiable concentrate:

The following substances are used to produce a 25% emulsifiable concentrate:
  25 parts of active substance,
  2.5 parts of epoxidised vegetable oil,
  10 parts of an alkylarylsulfonate/fatty alcohol polyglycol ether mixture,
  5 parts of dimethylformamide, and
  57.5 parts of xylene.

Emulsions of the desired concentration can be prepared from these concentrates by dilution with water.

Post-emergence antidote test in nutrient solution

General procedure

Plastic flower pots (upper diameter 6 cm), which have a pierced bottom, are filled with Zonolite and the cultivated seeds are sown therein. The pot is placed into a second transparent plastic flower pot (upper diameter 7 cm) in which there is 50 ml of water, which rises by capillary attraction and wets the seeds. From the 5th day the continuous loss of water is compensated with Hewitt nutrient solution. From the 15th day, when the cultivated plants are in the 1½- to 2-leaf stage, there is added to the nutrient solution, made up again to 50 ml, 10 ppm of the antidote to be tested + the amount of herbicide given below. From the 16th day, the loss of liquid is again made up with pure Hewitt nutrient solution. During the entire duration of the test, the temperature is 20°–23° C. with a relative humidity of 60–70%. Three weeks afer addition of the herbicide and antidote, an evaluation is made on the basis of a linea scale from 1 to 9, with 1 signifying total plant destruction, and 9 an unimpaired condition of health of the cultivated plants.

Test variants (1) 15 ppm of α-[4-(3,5-dichloropyridyl-2-oxy)-phenoxy]-propionic acid propargyl thiol ester in wheat of the "Zenith" variety;

(2) 4 ppm of 4-ethylamino-6-tert-butylamino-2-chloro-s-triazine in wheat of the "Zenith" variety;

(3) 2 ppm of α-[4-(p-trifluoromethylphenoxy)-phenoxy]-propionic acid-n-butoxyethyl ester in maize of the "Orla" variety;

(4) 8 ppm of α-[4-(p-trifluoromethylphenoxy)-phenoxy]-propionic acid-n-butoxyethyl ester in sorghum-millet of the "Funk G-522" variety;

(5) 4 ppm of Prometryne=2,4-bis-(isopropylamino)-6-methylthio-s-triazine in sorghum-millet of the "Funk G-522" variety; and (6) 8 ppm of α-[4-(3,5-dichloropyridyl-2-oxy)-phenoxy]-propionic acid methyl ester in wheat of the "Zenith" variety.

Compounds of the formula I have a good antidote action in these tests. The following results are given as examples:

| Test variant | Compound No. | Rating of the herbicidal effect (without/with antidote) |
| --- | --- | --- |
| 1 | 91 | 6/8 |
| 6 | 54 | 3/7 |
| 6 | 372 | 2/5 |

Pre-emergence antidote test in nutrient solution

A Hewitt nutrient solution is prepared, which contains the amount of herbicide given below and 10 ppm of the antidote to be tested.

There is used cultivated seed which could be expected to suffer damage from the employed herbicide at the given test concentration, and the seed is sown in granulated Zonolite (=expanded vermiculite) which is contained in a plastic flower pot having a pierced bottom (upper diameter 6 cm). This pot is placed into a second transparent plastic flower pot (upper diameter 7 cm), in which there is about 50 ml of the nutrient solution that has been prepared with herbicide and antidote; this solution then rises by capillary attraction in the filler material of the smaller pot and wets the seed and germinating plants. The loss of liquid is made up daily with pure Hewitt nutrient solution to 50 ml. Three weeks after commencement of the test, an evaluation is made on the basis of a linear scale from 1 to 9, with the rating 1 signifying total plant destruction, and the rating 9 signifying an unimpaired condition of health of the plants. The control solution used in a parallel test contains no antidote addition.

There are used the following:

(1) 4 ppm of Prometryne=2,4-bis-(isopropylamino)-6-methylthio-s-triazine in sorghum-millet of the "Funk G-522" variety;

(2) 4 ppm of 4-ethylamino-6-tert-butylamino-2-chloro-s-triazine in wheat of the "Farnese" variety;
(3) 4 ppm of α-[4-(p-trifluoromethylphenoxy)-phenoxy]-propionic acid-n-butoxyethyl ester in barley of the "Mazurka" variety;
(4) 5 ppm of Metolachlor=N-(1-methyl-2-methoxy-ethyl)-N-chloroacetyl-2-ethyl-6-methylaniline in sorgum-millet of the "Funk G-522" variety; and
(5) 1 ppm of 2-methoxy-4,6-bis-(γ-methoxy-propylamino)-s-triazine in sugar beet of the "Kleinwanzleben" variety.

Compounds of the formula I exhibited in these tests a good antidote action. The following results may be given as examples:

| Test variant | Compound No. | Rating of the herbicidal effect (without/with antidote) |
|---|---|---|
| 2 | 73 | 2/5 |
| 4 | 93 | 2/5 |
| 4 | 396 | 2/5 |
| 4 | 4 | 3/7 |
| 4 | 19 | 2/6 (with 1 ppm antidote concentration) |
| 5 | 19 | 2/5 |
| 5 | 36 | 1/5 |
| 3 | 96 | 2/5 |
| 5 | 112 | 1/7 (with 1 ppm antidote concentration) |
| 4 | 52 | 2/5 |
| 4 | 51 | 2/5 |

Antidote test with seed soaking

Rice seeds of the IR 8 variety are saturated during 48 hours with solutions of the test substances of 10 or 100 ppm concentration. The seeds are subsequently allowed to dry for about 2 hours, until they no longer stick together. Rectangular plastic pots (8×8 cm, 10 cm in height) are filled up to within 2 cm of the edge with sandy loam. In each pot is sowed 4 g of seed, and the seed is only very slightly covered (about the diameter of a seed). The soil is maintained in a moist (not boggy) condition. There is then applied either the herbicide N-(1-methyl-2-methoxyethyl)-N-chloroacetyl-2-ethyl-6-methylaniline or N-propoxyethyl-N-chloroacetyl-2,6-diethylaniline in dilute solution and in an amount which converted corresponds to 1.5 kg of active substance per hectare. An evaluation is made 18 days after planting on the basis of a linear scale from 1 to 9, according to which the rating 1 signifies total plant destruction, and the rating 9 an unimpaired condition of health of the plants.

Compounds of the formula I exhibit in this test a good antidote action. The following results may be given as examples:

|  | Compound No. | Rating of the herbicidal effect (without/with antidote) |
|---|---|---|
| 100 ppm | 396 | 2/5 |
|  | 397 | 2/5 |
| 10 ppm | 90 | 1/4 |
|  | 138 | 2/5 |

Pre-emergence antidote test (basic test)

General procedure

Small flower pots (upper diameter 6 cm) are filled with garden soil, into which the cultivated plants are sown, covered over and lightly pressed down. The substance to be tested as antidote is then sprayed on as a diluted solution (obtained from a wettable powder) in an amount corresponding to 4 kg of active substance per hectare. The herbicide is afterwards sprayed on in a similar manner. After a standing time of 18 days at about 20°–23° C. with 60–70% relative humidity, an evaluation is made on the basis of a linear scale from 1 to 9, according to which the rating 1 signifies total plant destruction, and the rating 9 an unimpaired condition of health of the cultivated plants. Plants without antidote protection are used in control tests.

The following are used:
(1) 1.5 kg of active substance per hectare of α-[4-(p-trifluoromethylphenoxy)-phenoxy]-propionic acid-n-butoxy-ethyl ester in maize of the "Orla 264" variety;
(2) 1.5 kg of active substance per hectare of Metolachlor=N-(1-methyl-2-methoxyethyl)-N-chloroacetyl-2-ethyl-6-methylaniline in sorghum-millet of the "Funk G-522" variety;
(3) 2.0 kg of active substance per hectare of Prometryne=2,4-bis-(isopropylamino)-6-methylthio-s-triazine in soya bean;
(4) 2.0 kg of active substance per hectare of 4-ethylamino-6-tert-butylamino-2-chloro-s-triazine in wheat of the "Farnese" variety;
(5) 4.0 kg of active substance per hectare of Prometryne=2,4-bis-(isopropylamino)-6-methylthio-s-triazine in sorghum-millet of the "Funk G-522" variety;
(6) 2.0 kg of active substance per hectare of α-14-(p-trifluoromethylphenoxy)-phenoxy]-propionic acid-n-butoxyethyl ester in barley of the "Mazurka" variety; and
(7) 1.0 kg of active substance per hectare of N-methoxy-ethyl-N-chloroacetyl-2,6-dimethylaniline in maize of the "Anjou 196" variety.

Compounds of the formula I exhibit in these tests a good antidote action. The following results are given as examples.

| Test variant | Comp. No. | Rating of the herbicidal effect without/with antidote |
|---|---|---|
| 6 | 138 | 4/7 |
| 5 | 398 | 1/4 |
| 4 | 31 | 2/4 |
| 7 | 51 | 2/5 |
| 3 | 378 | 2/5 |

Antidote action on transplanted rice with separate application (antidote pre-emergence+herbicide post-emergence)

Plastic pots (8×8 cm, 10 cm in height) are filled to within 2 cm of the edge with soil in the boggy-wet condition. The substance to be tested as antidote is sprayed in dilute solution, onto the surface, in an amount corresponding to 4 kg of active substance per hectare. Rice plants of the "IR-8" variety in the 1½- to 2-leaf stage are transplanted into the pots prepared in this manner. The water level is raised to about 1.5 cm on the next day. Four days after transplanting, there is added to the water 2-ethylamino-4-(1,2-dimethyl-n-propylamino)-6-methylthio-s-triazine in granular form in an amount which, when converted, corresponds to 0.75 kg of active substance per hectare. The temperature during the duration of the test is 26°–28° C., and the relative humidity is 60–80%. Twenty days after treatment with the herbicide, an evaluation is made based on a linear scale from 1 to 9, the rating 1 signifying total plant destruction, and the rating 9 unimpaired condition of health of the cultivated plants. Plants without antidote protection are used in control tests.

Compounds of the formula I exhibit in this test a good antidote action. The results below are given as examples.

| Comp. No. | Rating of the herbicidal effect (without/with antidote) |
|---|---|
| 396 | 3/6 |
| 42 | 5/7 |

I claim:
1. A compound of the formula

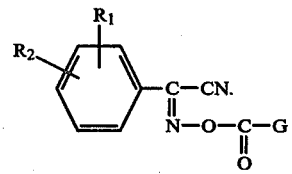

wherein
R$_1$ is hydrogen or halogen,
R$_2$ is hydrogen, halogen, lower alkyl or trifluoromethyl and
G is lower alkoxy, lower alkylthio, lower alkoxyalkoxy, lower haloalkoxy or phenoxy optionally substituted by halogen, methoxy or nitro.

2. A compound according to claim 1 in which R$_1$ and R$_2$ are hydrogen, and G is $\beta,\beta,\beta$-trichloroethoxy.

3. A compound according to claim 1 in which R$_1$ and R$_2$ are chlorine, and G is ethylthio.

4. A method for protecting cultivated plants from being damaged by harmful agricultural chemicals selected from the group consisting of triazines, haloacetanilides and pyridyloxyphenoxypropionates, which method comprises applying to said plants, to parts thereof or to the locus of their growth, an antidotally effective amount of a compound according to claim 1.

5. The method according to claim 4 in which, in the compound, R$_1$ and R$_2$ are hydrogen, and G is $\beta,\beta,\beta$-trichloroethoxy.

* * * * *

UNITED STATES PATENT AND TRADEMARK OFFICE
CERTIFICATE OF CORRECTION

PATENT NO.  : 4,475,945

DATED       : October 9, 1984

INVENTOR(S) : Henry Martin

It is certified that error appears in the above-identified patent and that said Letters Patent is hereby corrected as shown below:

On the cover page, Item 60, Line 3 should read--

Aug. 30, 1978, abandoned --.

Signed and Sealed this

First Day of October 1985

[SEAL]

*Attest:*

*Attesting Officer*

DONALD J. QUIGG

*Commissioner of Patents and Trademarks—Designate*